United States Patent
Wang et al.

(10) Patent No.: US 9,266,990 B2
(45) Date of Patent: Feb. 23, 2016

(54) METHOD FOR PRODUCING POLYOXYMETHYLENE DIMETHYL ETHERS

(71) Applicants: Shandong Yuhuang Chemical Co., Ltd., Shandong Province (CN); Tsinghua University, Beijing (CN)

(72) Inventors: Jinfu Wang, Beijing (CN); Yanyan Zheng, Beijing (CN); Shengwei Wang, Shandong Province (CN); Tiefeng Wang, Beijing (CN); Shuangxi Chen, Shandong Province (CN); Cunfu Zhu, Shandong Province (CN)

(73) Assignees: SHANDONG YUHUANG CHEMICAL CO., LTD., Shandong Province (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 14/601,787

(22) Filed: Jan. 21, 2015

(65) Prior Publication Data

US 2015/0291722 A1    Oct. 15, 2015

(30) Foreign Application Priority Data

Apr. 11, 2014    (CN) .......................... 2014 1 0146196

(51) Int. Cl.
| | |
|---|---|
| *C08G 16/02* | (2006.01) |
| *C07C 41/36* | (2006.01) |
| *C07C 41/09* | (2006.01) |
| *C07C 41/01* | (2006.01) |
| *C07C 41/14* | (2006.01) |

(52) U.S. Cl.
  CPC ............ *C08G 16/0225* (2013.01); *C07C 41/01* (2013.01); *C07C 41/09* (2013.01); *C07C 41/14* (2013.01); *C07C 41/36* (2013.01)

(58) Field of Classification Search
  None
  See application file for complete search history.

(56) References Cited

U.S. PATENT DOCUMENTS

| 2,449,469 | A | * | 9/1948 | Gresham et al. ............... 568/601 |
| 5,746,785 | A | | 5/1998 | Moulton et al. |
| 5,959,156 | A | | 9/1999 | Hagen et al. |
| 6,160,174 | A | | 12/2000 | Hagen et al. |
| 6,160,186 | A | | 12/2000 | Hagen et al. |
| 6,392,102 | B1 | | 5/2002 | Hagen et al. |
| 7,560,599 | B2 | | 7/2009 | Chen et al. |
| 7,671,240 | B2 | | 3/2010 | Stroefer et al. |
| 7,700,809 | B2 | | 4/2010 | Stroefer et al. |
| 2007/0260094 | A1 | | 11/2007 | Schelling et al. |
| 2010/0056830 | A1 | | 3/2010 | Chen et al. |

FOREIGN PATENT DOCUMENTS

| CN | 102701923 A | 10/2012 |
| CN | 103360224 A | 10/2013 |
| CN | 103626640 A | 3/2014 |

OTHER PUBLICATIONS

Database CAPLUS in STN, Acc. No. 2013:1875622, Gao et al., CN 103420817 A (Dec. 4, 2013) (abstract).*
Database CAPLUS in STN, Acc. No. 2012:1713643, Li et al., CN 102786397 A (Nov. 21, 2012) (abstract).*
"Fluidized Bed Reactor and Method for Preparing Polyoxymethlyene Dimethyl Ethers from Dimethoxymethane and Paraformaldehyde," Inventors: Jinfu Wang, Qiang Tang, Shengwei Wang, Tiefeng Wang, Shuangxi Chen, and Yuqiang Wang, U.S. Appl. No. 14/589,651, filed Jan. 5, 2015.
International Search Report and Written Opinion regarding Application No. PCT/CN2015/075079, dated Mar. 7, 2015. English-language translation is not available.

* cited by examiner

*Primary Examiner* — Brian J Davis
(74) *Attorney, Agent, or Firm* — Harness, Dickey & Pierce, P.L.C.

(57) ABSTRACT

A method for producing polyoxymethylene dimethyl ethers using fluidized bed reactor is provided. The fluidized bed reactor gives high conversion of feedstock during synthesis of polyoxymethylene dimethyl ethers. The product separation process includes pre-rectification, extractive rectification and vacuum rectification in series. In the pre-rectification process, the side-draw fraction $PODE_2$ is recycled into the fluidized bed reactor, thus product distribution and selectivity to target components in the reactor can be improved. The extractive rectification process realizes coupling of neutralization, extraction, recovery of unconverted feedstock and products separation, thus significantly simplifies the process. The method for preparation of polyoxymethylene dimethyl ethers in this invention is simple, and has high conversion of feedstock, low energy cost and high selectivity to products.

20 Claims, 1 Drawing Sheet

METHOD FOR PRODUCING POLYOXYMETHYLENE DIMETHYL ETHERS

CROSS REFERENCE TO RELATED APPLICATIONS

The present application is based on, and claims priority from, Chinese application number 201410146196.5, filed on Apr. 11, 2014, the disclosure of which is hereby incorporated by reference herein in its entirety.

FIELD OF THE INVENTION

The invention generally relates to a process for producing oxygenated compounds, in particular relates to a continuous process for producing polyoxymethylene dimethyl ethers which can be used as diesel fuel additives to reduce smoke and engine exhaust emissions during combustion.

TECHNICAL BACKGROUND

With the development of city, the amount of vehicles has increased significantly. The emissions from vehicles have become an important cause of air pollution such as haze. Due to high boiling point and low H/C mass ratio, the smoke and soot formation (including particulate matter, nitrogen oxides, CO, etc.) of diesel is more serious than that of gasoline during combustion. In order to reduce the air pollution caused by vehicles, it is important to upgrade the combustion performance of diesel.

Oxygenated compounds with few or no C—C bonds can greatly improve the efficiency of diesel combustion and reduce smoke and soot formation when added to conventional diesel fuel. A large number of oxygenated chemicals like ethers, acetals, alcohols and lipids have been widely studied to be used as diesel fuel additives. However, no oxygenates have been widely applied because they do not meet the ideal characteristics of an oxygenated compound to blend with diesel which includes an adequate cetane number, a high boiling point to satisfy the flash point specifications, a low condensation point to guarantee good cold flow properties, being miscible with various types of diesel fuels and a suitable density. Other properties like toxicity, biodegradability, environmental friendliness, sustainability, raw material adequacy and so on should also be strictly taken into consideration.

Besides air pollution, oil resources exhaustion is another issue that needed to be addressed as a matter of urgency. Finding alternative energy sources to replace the depleting oil resources is imperative. With the advantage of abundant source, environmental friendliness and being easy to store and transport, methanol is considered to be the best alternative energy sources. Rich in coal but poor in natural gas, China has pioneered the development of coal-based methanol economy and C1 chemicals like methanol and formaldehyde is facing serious oversupply in recent years while diesel often encounters short supply due to crude oil shortage and seasonally soared consumption. Therefore synthesis of oxygenated compounds as diesel fuel additives from methanol is of great interest. This can fully utilize the large surplus C1 chemicals and alleviate the diesel supply crisis, and can bring enormous economic and environmental benefits.

Methanol, together with dimethyl ether and dimethoxymethane produced from C1 chemicals have all been considered to be used as diesel fuel additives. However, Methanol has the disadvantages of low solubility in diesel and low cetane number. Dimethyl ether has a high cetane number, but its addition to diesel increases the vapor pressure and lowers the viscosity. Especially, dimethoxymethane (DMM) with the ability to significantly reduce smoke and engine exhaust emissions, has drawn much attention. However, DMM has a low cetane number and is prone to cause vapor lock. Therefore, methanol, DME and DMM are difficult for wide use as diesel fuel additives.

Moulton et al. disclosed in U.S. Pat. No. 5,746,785A that the fuel containing the mixed polyoxymethylene dimethyl ethers ($PODE_n$) blend component is safer to handle and use than fuel containing the same amount of dimethoxymethane. It was also found that in comparison with the diesel fuel containing dimethoxymethane alone as a blended component, the diesel fuel containing mixed $PODE_n$ is less volatile, has a higher flash point, has a higher viscosity closer to that of conventional diesel fuels and has higher fuel lubricity. All these properties make $PODE_n$ ideal diesel fuel additives.

$PODE_n$ ($CH_3O(CH_2O)_nCH_3$) refers to a homologous series of oxygenated compounds. Among the $PODE_n$ compounds, $PODE_2$ does not satisfy the security criterion due to its low flash point, and $PODE_{n>5}$ will precipitate at low temperatures due to high melting point. The $PODE_{3-5}$ compounds are most ideal diesel additives because their physical properties are consistent with those of diesel fuels and the oxygen content (~50%) and cetane number (70 to 100) are high. Directly blending the diesel fuel with 20% (v/v) $PODE_{3-5}$ can improve the combustion efficiency of fuel while at the same time alleviate the diesel short supply, bringing important environmental and economic benefits.

Some processes have been proposed for preparation of polyoxymethylene dimethyl ethers $PODE_n$.

U.S. patent references U.S. Pat. No. 5,959,156A, U.S. Pat. No. 6,160,174A, U.S. Pat. No. 6,160,186A, U.S. Pat. No. 6,392,102B1 by British Petroleum (BP) describe a process in which methanol or dimethyl ether is converted to formaldehyde via oxidative dehydrogenation, and then formaldehyde reacts with methanol or dimethyl ether forming dimethoxymethane and polyoxymethylene dimethyl ethers. The process is very complex, comprising unit operations including oxidative dehydrogenation, adsorption cooling, catalytic distillation, neutralization and separation. The selectivity to PODE.sub.n>1 in polyoxymethylene dimethyl ethers is less than 10%.

U.S. patent references U.S. Pat. No. 7,700,809B2, US20070260094A1, and U.S. Pat. No. 7,671,240B2 by BASF describe the preparation of polyoxymethylene dimethyl ethers from dimethoxymethane and trioxane in the presence of acidic catalyst. The selectivity to PODE.sub.3.about.5 in polyoxymethylene dimethyl ethers is about 20 wt %, owing to the low water content in system (<1%). However, the cost of highly purified trioxane and dimethoxymethane is too high. Besides, a considerable amount of by-products PODE.sub.n>5 are produced, thus complicating the separation process.

U.S. patent references US20100056830 A1 and U.S. Pat. No. 7,560,599B2 by Lanzhou Institute of Chemical Physics, Chinese Academy of Sciences, describe the preparation of polyoxymethylene dimethyl ethers from methanol and trioxane in the presence of acidic ionic liquid. The conversion of trioxane could reach 90%. However, ionic liquid is unfavorable due to high cost, difficult separation and recycling, thus complicating the process.

Chinese patent application publication of CN103360224A by Runcheng Carbon Material Technology Co. Ltd in Dongying, China, describes a process for producing polyoxymethylene dimethyl ethers. In this process, the reactants are circulated in the reactor and membrane separation device, aiming for 100% conversion of formaldehyde. However, the energy cost of this process is huge. The attempt to reach 100% conversion of formaldehyde is hard to realize due to the reversibility of the reactions forming polyoxymethylene dimethyl ethers.

Chinese patent application publication of CN102701923A by Beijing Coreteam Engineering & Technology Co. Ltd., describes a process for preparation of polyoxymethylene dimethyl ethers from methanol and trioxane using ionic liquid as catalyst in a cannula reactor. The process is very complex, comprising the reaction unit, vacuum flashing unit, extraction unit, alkali washing unit, and rectification unit. In this process, the yield of target product is low while the ionic liquid catalyst is hard to recycle. In the alkali washing unit, alkali could react with the unconverted formaldehyde, thus increasing feedstock cost.

SUMMARY OF THE INVENTION

It is an object of the invention to develop a novel method to overcome the above drawbacks.

According to one aspect of the present invention, a method for preparation of polyoxymethylene dimethyl ethers from dimethoxymethane and paraformaldehyde using solid acid as catalyst in a fluidized bed reactor is provided, comprising the steps of:

(1) Synthetic Reaction Unit:

Feeding dimethoxymethane and paraformaldehyde into a fluidized bed reactor loaded with solid acid catalyst. The dimethoxymethane and paraformaldehyde contact with solid acid catalyst and react, and produce reaction mixture of $PODE_k$ (k>1);

(2) Product Separation Unit:

Including pre-rectification, extractive rectification and vacuum rectification; during the pre-rectification, the reaction mixture from the fluidized bed reactor is fed into a pre-rectifying column and separated into overhead fraction dimethoxymethane, side-draw fraction $PODE_2$ and heavy fraction comprising $PODE_{n>2}$, unconverted formaldehyde and some by-products. A portion of overhead fraction dimethoxymethane is recycled into the fluidized bed reactor and the left is refluxed into the pre-rectifying column. The side-draw fraction $PODE_2$ is recycled into the fluidized bed reactor. During the extractive rectification, the heavy fraction comprising $PODE_{n>2}$ is fed into top of an extractive rectifying column and contact with the extraction solvent. The unconverted formaldehyde and by-products such as alcohol enter the extract phase. The extract phase is regenerated for separation of the extraction solvent and the unconverted formaldehyde for recycling. During the vacuum rectification, the raffinate phase is fed into the vacuum rectifying column and separated into overhead fraction $PODE_{3\sim m}$ and heavy fraction $PODE_{(m+1)\sim n}$. $PODE_{3\sim m}$ are the target components, wherein m is an integer larger than 3, and determined by actual demand, and n is an integer bigger than m+1.

The feeding method of dimethoxymethane and paraformaldehyde could be: feeding dimethoxymethane and paraformaldehyde into pulping tank, pulping the reactants mixture and then pumping the mixture into the fluidized bed reactor. The feeding method could also be: pumping the dimethoxymethane into the fluidized bed reactor, feeding solid paraformaldehyde into the fluidized bed reactor by switching screw feeders using at least two screw feeders. The continuous feeding of solid feedstock helps realizing the large-scale industrialization production of polyoxymethylene dimethyl ethers from dimethoxymethane and paraformaldehyde using solid acid as catalyst.

The dimethoxymethane to paraformaldehyde mass ratio is in the range of 10:1 to 1:2.

Compared with a cannula reactor, the fluidized bed reactor improves dispersion uniformity of catalyst and conversion of formaldehyde. The process according to the present invention could realize industrialized production of polyoxymethylene dimethyl ethers. The fluidized bed reactor could be multi-stage, which could improve the product distribution in polyoxymethylene dimethyl ethers owing to the stripping effect of interstage component.

In the synthetic reaction unit, the solid catalyst concentration in the fluidized bed reactor could be 5%~30%, the operation temperature could be 30~120° C., the operation pressure could be 0.1~1 MPa, and the reaction temperature could be 0.5~6 hours.

The solid acid catalyst could be one or combination of cation exchange resin, molecular sieves and silica gel.

In the product separation unit, the pH value of the extraction agent should be controlled to be in the range of 7~9. Adjusting the pH to 7~9 facilitates separation and recycling of the unconverted formaldehyde, and facilitates the neutralization of acids, so that the products are stable in the alkalescent system.

In the product separation unit, the extraction agent could be one or combination of methanol, ethanol, water, benzene, acetone, aqueous solution of sodium sulfite or aqueous solution of alkali.

The value of m in the target components $PODE_{3\sim m}$ could be 4 or 5.

In the product separation unit, the pre-rectifying column is packed column or plate column, with 10~50 theoretical plates. The operation pressure of the pre-rectifying column could be 0~0.3 MPa (Gauge pressure). The column top temperature could be 40~65° C., while the column bottom temperature could be 120~150° C. The reflux ratio of overhead fraction dimethoxymethane could be 0.5~3. The left overhead fraction dimethoxymethane is recycled into the fluidized bed reactor. The side withdrawing position of $PODE_2$ could be the 6—9 plant under the column top. The side-draw fraction $PODE_2$ is recycled into the fluidized bed reactor. The bottom fraction is pumped into top of the extractive rectifying column and mixed with the extraction solvent. The operation column of the extractive rectifying column could be 0~0.3 MPa (Gauge pressure). The unconverted formaldehyde and by-products such as alcohol enter the extract phase. The extract phase is regenerated for separation of the extraction solvent and the unconverted formaldehyde for recycling.

In the product separation unit, the extractive rectifying column is packed column or plate column, with 10~40 theoretical plates. The column top temperature could be 90~120° C., while the column bottom temperature could be 120~150° C. The extractive agent to feedstock mass ratio could be 0.3~1.5. The pH value of the extractive agent could be in the range of 6~10. The bottom fraction in the extractive rectifying column is pumped into the vacuum rectifying column. The operation pressure of the vacuum rectifying column could be in the range of −0.06~−0.098 (Gauge pressure). In the vacuum rectifying column, the feedstock mixture is separated into overhead fraction target components $PODE_{3\sim m}$ and heavy fraction $PODE_{(m+1)\sim n}$. The vacuum rectifying column is packed column with 10~30 theoretical plates. The column top temperature could be 60~100° C., while the column bottom temperature could be 120~160° C.

The advantageous effects of this invention include simple process, high conversion of feedstock, low energy cost, high selectivity to products, and only trace amount of by-products produced in the whole process.

101—pulping tank; 102—fluidized bed reactor; 103—pre-rectifying column; 104-1, 104-2, 104-3—condensation heat exchanger; 105-1, 105-2, 105-3—reflux tank; 106-1, 106-2, 106-3—reboiler; 107—extraction rectifying column; 108—vacuum rectifying column.

Figure 2:
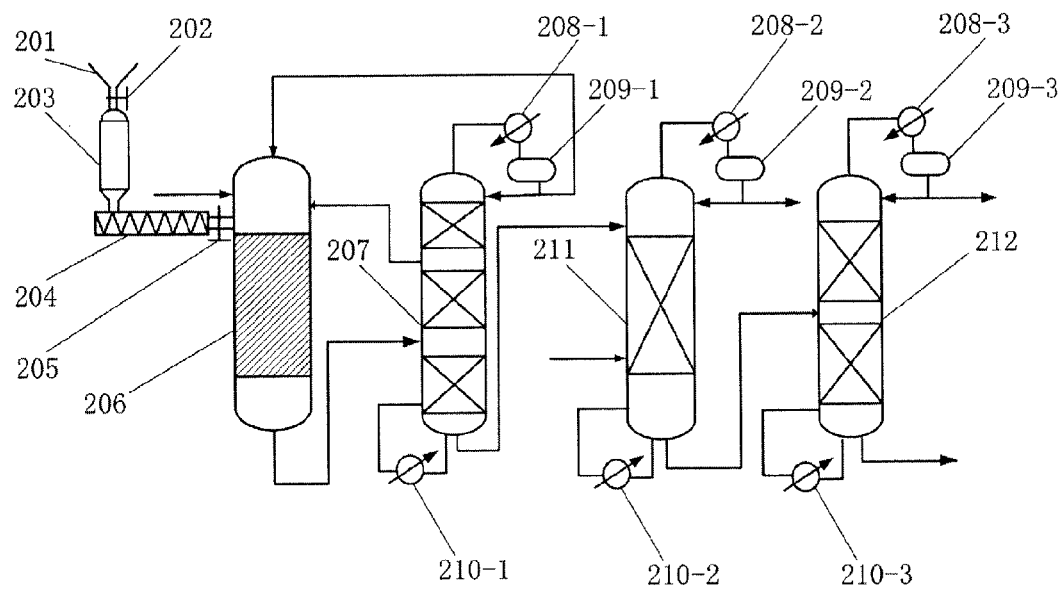

FIG. 2 is a diagram illustrating a process for preparation of polyoxymethylene dimethyl ethers from dimethoxymethane and paraformaldehyde using screw feeding method.

201—charging opening of paraformaldehyde; 202—charging control valve of paraformaldehyde; 203—storage tank of paraformaldehyde; 204—screw feeder; 205—feeding control valve of paraformaldehyde; 206—fluidized bed reactor; 207—pre-rectifying column; 208-1, 208-2, 208-3—condensation heat exchanger; 209-1, 209-2, 209-3—reflux tank; 210-1, 210-2, 210-3—reboiler; 211—extraction rectifying column; 212—vacuum rectifying column.

DETAILED DESCRIPTION OF EMBODIMENTS

In accordance with an embodiment of the invention, a method for preparation of polyoxymethylene dimethyl ethers from dimethoxymethane and paraformaldehyde using solid acid as catalyst is provided, comprising the steps of:

(1) Synthetic Reaction Unit

Dimethoxymethane and paraformaldehyde are fed into a fluidized bed reactor loaded with solid acid catalyst. Dimethoxymethane and paraformaldehyde contact with solid acid catalyst and react, and produce reaction mixture of $PODE_k$ (k>1).

(2) Product Separation Unit

The product separation unit includes pre-rectification, extractive rectification and vacuum rectification.

During the pre-rectification, the reaction mixture from the fluidized bed reactor is fed into a pre-rectifying column and separated into overhead fraction dimethoxymethane, side-draw fraction $PODE_2$ and heavy fraction comprising $PODE_{n>2}$, unconverted formaldehyde and some by-products. A portion of the overhead fraction dimethoxymethane is recycled into the fluidized bed reactor and the left is refluxed into the pre-rectifying column. The side-draw fraction $PODE_2$ is recycled into the fluidized bed reactor.

During the extractive rectification, the heavy fraction is fed into top of an extractive rectifying column and contact with the extraction solvent. The unconverted formaldehyde and by-products such as alcohol enter the extract phase. The extract phase is regenerated for separation of the extraction solvent and the unconverted formaldehyde for recycling.

During the vacuum rectification, the raffinate phase is fed into the vacuum rectifying column and separated into overhead fraction $PODE_{3-m}$ and heavy fraction $PODE_{(m+1)-n}$. $PODE_{3-m}$ are the target components, wherein m is an integer bigger than 3, and determined by actual demand, and n is an integer bigger than m+1.

In one embodiment, the fluidized bed reactor, in which dimethoxymethane and paraformaldehyde react over solid acid catalyst, could use the fluidized bed reactor and method disclosed in U.S. application Ser. No. 14/589,651 by Jinfu Wang, Qiang Tang et. al. Herein, the disclosure of U.S. application Ser. No. 14/589,651 is incorporated by reference herein in its entirety.

In one embodiment, solid acid catalyst is loaded into the fluidized bed reactor until the solid catalyst concentration reaches 5%~30%, preferably 15%~30%. The solid acid catalyst could be one selected from the group of cation exchange resin, molecular sieves and silica gel, or the combination thereof.

The dimethoxymethane to paraformaldehyde mass ratio is in the range of 10:1 to 1:2, preferably 5:1 to 1:2. The feeding method of dimethoxymethane and paraformaldehyde could be feeding dimethoxymethane and paraformaldehyde into pulping tank, pulping the reactants mixture and then pumping the mixture into the fluidized bed reactor. The feeding method could also be pumping the dimethoxymethane into the fluidized bed reactor, feeding solid paraformaldehyde into the fluidized bed reactor by switching screw feeders using at least two screw feeders.

Inert gas or superheated steam of dimethoxymethane could be used as the fluidizing gas of the fluidized bed, and can be input into the bed from the bottom of the fluidized bed. Using the reactant dimethoxymethane as fluidizing gas could significantly decrease amount of by-products and enhance conversion of reactants.

The reactor could be maintained isothermal (for example at 90° C.) by feeding isothermal hot water (for example at 90° C.) into the jacketed heat exchanger outside the reactor wall and isobaric (for example at 0.3 MPa). This is only an example, not as a limit, actually liquid at other temperature can be inputted into the jacketed heat exchanger to maintain the bed at the other temperature.

Compared with a cannula reactor, the fluidized bed reactor improves dispersion uniformity of catalyst and reactants, and enhances the conversion of formaldehyde.

In one example, the fluidized bed reactor could be multistage, which could improve the product distribution in polyoxymethylene dimethyl ethers owing to the stripping effect of interstage component.

In one example, the reaction temperature of the fluidized bed reactor could be 30° C.~120° C., preferably 90° C.~110° C., the operation pressure could be 0.1 MPa~1 MPa, preferably 0.5 MPa~0.8 MPa, the reaction time could be 0.5~6 hours, preferably 2~4 hours.

In the product separation unit, the pre-rectifying column is packed column or plate column, with 10~50, preferably 20~40, theoretical plates. The operation pressure of the pre-rectifying column could be 0~0.3 MPa (Gauge pressure), preferably 0.1~0.3 MPa (Gauge pressure). The column top temperature could be 40~65° C., preferably 50~65° C. The reflux ratio of overhead fraction dimethoxymethane could be 0.5~3, preferably 1~3. The left portion of the overhead fraction dimethoxymethane is recycled into the fluidized bed reactor. The side withdrawing position of $PODE_2$ could be the 6~9, preferably 7~8, plant under the column top. The side-draw fraction $PODE_2$ is recycled into the fluidized bed reactor, so as to improve the product distribution and selectivity to target components in the reactor. The heavy fraction comprising $PODE_{n>2}$, unconverted formaldehyde and by-products is drawn from the column bottom. The column bottom temperature could be 120~150° C., preferably 140~150° C. The bottom fraction is pumped into top of the extractive rectifying column and mixed with the extraction solvent.

The operation pressure of the extractive rectifying column could be 0~0.3 MPa (Gauge pressure). The unconverted formaldehyde and by-products such as alcohol enter the extract phase. The extract phase is regenerated for separation of the extraction solvent and the unconverted formaldehyde for recycling. The extractive rectifying column is packed column or plate column, with 10~40 theoretical plates. The column top temperature could be 90~120° C., while the column bottom temperature could be 120~150° C. The extraction agent could be one or a combination of methanol, ethanol, water, benzene, acetone, aqueous solution of sodium sulfite or aqueous solution of alkali, preferably one or a combination of methanol, water, aqueous solution of alkali and benzene. The extractive agent to feedstock mass ratio could be 0.3~1.5. The pH value of the extractive agent could be in the range of 6~10, preferably 7~9.

Adjusting pH value of the extraction agent in the extractive rectification process realizes coupling of neutralization, extraction, recovery of unconverted feedstock and products separation. This significantly simplifies the process and saves the cost of equipment.

The bottom fraction in the extractive rectifying column is pumped into the vacuum rectifying column. The operation pressure of the vacuum rectifying column could be in the range of −0.06~−0.098 MPa (Gauge pressure). In the vacuum rectifying column, the feedstock mixture is separated into overhead fraction target components $PODE_{3-m}$ and heavy fraction $PODE_{(m+1)-n}$. It should be noted that the value of m is determined based on the climate conditions of the product using area. For example, in South China or summer in North China, m could be 5. While in winter in North China, m preferably adopts lower values, such as 4.

The vacuum rectifying column could be plate column or packed column. For example, the vacuum rectifying column is a packed column with 10~30 theoretical plates, column top temperature 90° C. and column bottom temperature 160° C.

In this invention, adjusting pH value of the extraction agent in the extractive rectification process realizes recovery of unconverted feedstock and products separation, and also neutralizes the acid introduced by feedstock to improve the storage stability of the products. The $PODE_k$ compounds are unstable in acidic condition. Previous technologies use alkali to neutralize the acid, but the alkali reacts with formaldehyde. In this example, the extraction agent with pH value 7~9 could realize neutralization of acid and avoid consumption of formaldehyde at the same time.

In this process for preparation of polyoxymethylene dimethyl ethers from dimethoxymethane and paraformaldehyde according to one embodiment, solid acid is a preferable catalyst. Compared with ionic liquid used in conventional technologies, solid acid has advantages including low cost, easy recycling, easy separation and simple process.

EXAMPLE 1

Figure 1:
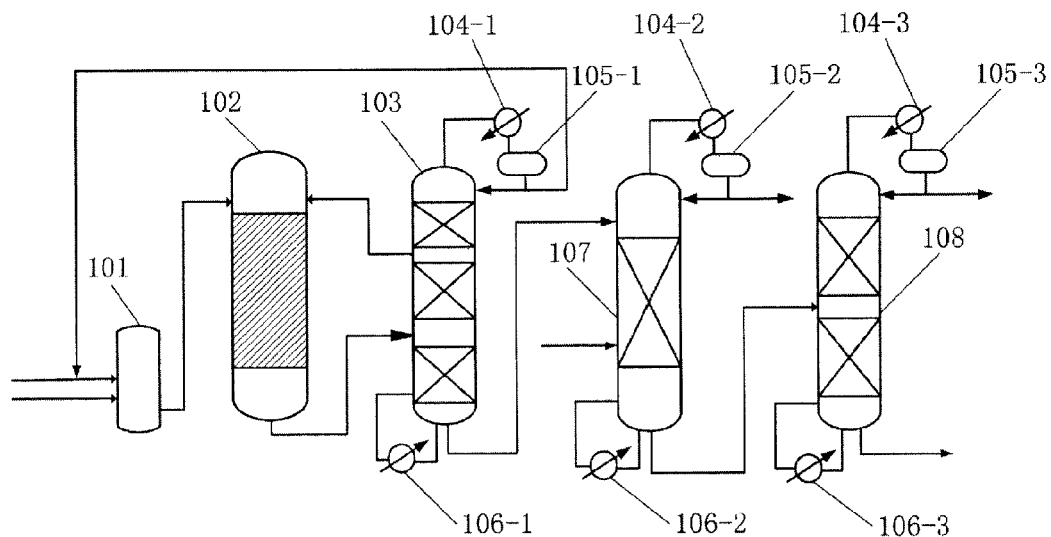
FIG. 1 is a diagram illustrating a process for preparation of polyoxymethylene dimethyl ethers from dimethoxymethane and paraformaldehyde using pulping feeding method.

As shown in FIG. 1, cation exchange resin is loaded into the fluidized bed reactor 102 until the solid catalyst concentration reaches 30%. The mixture of dimethoxymethane and paraformaldehyde with mass ratio 1:2 is pulped in the pulping tank 101. The pulp mixture of dimethoxymethane and paraformaldehyde is pumped into the fluidized bed reactor 102.

Superheated steam of dimethoxymethane at 100° C. is used as the fluidizing gas of the fluidized bed reactor 102, and is input into the reactor from the bottom of the reactor.

The reactor could be maintained isothermal at 90° C. by feeding isothermal hot water at 90° C. into the jacketed heat exchanger outside the reactor wall and the reactor could be maintained isobaric at 0.3 MPa. In a typical example, the reaction time is 4 hours. Of course, water is only provided as one example, in fact other liquid at the same or other temperature can be input into the jacketed heat exchanger, to maintain the bed isothermal at the same or other temperature.

In the product separation unit, the pre-rectifying column 103 is a packed column with 30 theoretical plates using ring packing material. The operation pressure of the pre-rectifying column 103 is 0.3 MPa (Gauge pressure). The column top temperature of the pre-rectifying column 103 is 65° C. The overhead fraction dimethoxymethane is condensed by the condensation heat exchanger 104-1 and collected in the reflux tank 105-1. The reflux ratio of overhead fraction dimethoxymethane is 2. The left portion of overhead fraction dimethoxymethane is recycled into the fluidized bed reactor 102. The side withdrawing position of $PODE_2$ is the 9th plant under the column top. The side-draw fraction $PODE_2$ is recycled into the fluidized bed reactor 102. The column bottom temperature of the pre-rectifying column 103 is 150° C. A portion of the bottom fraction from the pre-rectifying column 103 is vaporized by the reboiler 106-1. The left portion of the bottom fraction is pumped into top of the extractive rectifying column 107 and mixed with the extraction solvent. The operation pressure of the extractive rectifying column 107 is 0.3 MPa (Gauge pressure). The unconverted formaldehyde and by-products such as alcohol enter the extract phase. The extract phase is regenerated for separation of the extraction solvent and the unconverted formaldehyde for recycling. The extractive rectifying column 107 is a plate column with 30 theoretical plates. The column top temperature of the extractive rectifying column is 120° C., while the column bottom temperature is 150° C. The extraction agent for the extractive rectification process is aqueous solution of alkali with pH 8.0. The extractive agent to feedstock mass ratio is 1.5. Adjusting pH value of the extraction agent in the extractive rectification process realizes coupling of neutralization, extraction, recovery of unconverted feedstock and products separation. This significantly simplifies the process and saves the cost of equipment.

The bottom fraction in the extractive rectifying column 107 is pumped into the vacuum rectifying column 108. The operation pressure of the vacuum rectifying column 108 is −0.08 MPa (Gauge pressure). In the vacuum rectifying column 108, the feedstock mixture is separated into overhead fraction target components $PODE_{3-m}$ and heavy fraction $PODE_{(m+1)-n}$. In this example, in is 5, but in can be adjusted according to actual need. The vacuum rectifying column 108 is a packed column with 30 theoretical plates, and its column top temperature is 90° C. and column bottom temperature is 160° C.

Analysis shows that the overhead fraction of the vacuum rectifying column 108 contains about 98 wt % $PODE_{3-5}$, and little amount of $PODE_2$ and $PODE_6$.

EXAMPLE 2

As shown in FIG. 2, loading cation exchange resin into the fluidized bed reactor 206 until the solid catalyst concentration reaches 25%. Liquid dimethoxymethane is pumped into the fluidized bed reactor 206. Solid paraformaldehyde is continuously fed into the fluidized bed reactor 206 using two switchable screw feeders 204. The mass ratio of dimethoxymethane and paraformaldehyde is 1:2. Superheated steam of dimethoxymethane at 100° C. is used as the fluidizing gas of the fluidized bed reactor 206. The reactor could be maintained isothermal at 100° C. by feeding isothermal hot water at 100° C. into the jacketed heat exchanger outside the reactor wall and isobaric 0.35 MPa, but this is given just as a typical condition, in fact the reactor can be maintained at other temperature by feeding isothermal hot water or other isothermal hot liquid at the other temperature into the jacked heat exchanger. In a typical example, the reaction time is 3 hours.

In the product separation unit, the pre-rectifying column 207 is a packed column with 25 theoretical plates using saddle packing material for example. The operation pressure of the pre-rectifying column 207 is 0.25 MPa (Gauge pressure). The column top temperature of the pre-rectifying column 207 is 60° C. The reflux ratio of overhead fraction dimethoxymethane is 1.5. The left portion of the overhead fraction dimethoxymethane is recycled into the fluidized bed reactor 206. The side withdrawing position of $PODE_2$ is the 8th plant under the column top. The side-draw fraction $PODE_2$ is recycled into the fluidized bed reactor 206. The column bottom temperature of the pre-rectifying column 207 is 150° C. The bottom fraction from the pre-rectifying column 207 is pumped into top of the extractive rectifying column 211 and mixed with the extraction solvent. The operation pressure of the extractive rectifying column 211 is 0.28 MPa (Gauge pressure). The unconverted formaldehyde and by-products such as alcohol enter the extract phase. The extract phase is regenerated for separation of the extraction solvent and the unconverted formaldehyde for recycling. The extractive rectifying column 211 is a plate column with 35 theoretical plates. The column top temperature of the extractive rectifying column 211 is 110° C., while the column bottom temperature of the extractive rectifying column 211 is 140° C. The extraction agent is pure water. The extractive agent to feedstock mass ratio is 1.5. The bottom fraction in the extractive rectifying column 211 is pumped into the vacuum rectifying column 212. The operation pressure of the vacuum rectifying column 212 is −0.06 MPa (Gauge pressure). In the vacuum rectifying column 212, the feedstock mixture is separated into overhead fraction target components $PODE_{3\sim m}$ and heavy fraction $PODE_{(m+1)\sim n}$, in this example, m is 4. The vacuum rectifying column 212 is a packed column with 35 theoretical plates, and its column top temperature is 80° C. and its column bottom temperature is 140° C.

Analysis finds that the overhead fraction of the vacuum rectifying column 212 contains about 97 wt % $PODE_{3\sim 5}$, and little amount of $PODE_2$ and $PODE_6$.

The method for production of polyoxymethylene dimethyl ethers according to this embodiment has advantages including simple process, continuous operation and being easy to scale-up. The feeding method uses at least two switchable feeders for effectively feeding of solid paraformaldehyde, thus makes it possible for using solid as an effective feedstock. The fluidized bed reactor facilitates temperature control and contact between reactants and catalyst, thus significantly enhances the conversion of feedstock and selectivity. The product separation unit includes pre-rectification, extractive rectification and vacuum rectification, and could effectively improve the separation of unconverted formaldehyde. The products polyoxymethylene dimethyl ethers could improve the combustion efficiency of diesel and decrease emission of waste, thus could relieve, at least to some degree, energy crisis in China or other countries.

What is claimed is:

1. A method for producing polyoxymethylene dimethyl ethers, the method comprising:
    conducting a synthetic reaction process including:
        feeding dimethoxymethane and paraformaldehyde into a fluidized bed reactor, and
        contacting the dimethoxymethane and paraformaldehyde with a solid acid catalyst to produce a reaction mixture of $PODE_k$, wherein k is an integer bigger than 1;
    conducting a product separation process including:
        a pre-rectification, an extractive rectification and a vacuum rectification; during pre-rectification:
            feeding the reaction mixture from the fluidized bed reactor into a pre-rectifying column and separating the reaction mixture into an overhead fraction of dimethoxymethane, a side-draw fraction of $PODE_2$ and a heavy fraction of $PODE_{n>2}$, unconverted formaldehyde and by-products, recycling a first portion of the overhead fraction of dimethoxymethane into the fluidized bed reactor,
            refluxing a second portion of the overhead fraction of dimethoxymethane into the pre-rectifying column, and
        recycling the side-draw fraction of $PODE_2$ into the fluidized bed reactor;
        during the extractive rectification:
            feeding the heavy fraction of $PODE_{n>2}$ into the top of an extractive rectifying column,
            contacting the heavy fraction of $PODE_{n>2}$ with an extraction solvent,
            entering the unconverted formaldehyde and by-products into an extract phase, and
            regenerating the extract phase to separate the extraction solvent and the unconverted formaldehyde for recycling; and
        during the vacuum rectification:
            feeding a raffinate phase from the bottom of the extractive rectifying column into the vacuum rectifying column, and
            separating the raffinate phase into an overhead fraction of $PODE_{3\sim m}$ and a heavy fraction of $PODE_{(m+1)\sim n}$, wherein m is an integer bigger than 3 and n is an integer bigger than m+1.

2. The method for producing polyoxymethylene dimethyl ethers according to claim 1, wherein feeding dimethoxymethane and paraformaldehyde includes feeding dimethoxymethane and paraformaldehyde into a pulping tank, pulping the reaction mixture into a pulped mixture and then pumping the pulped mixture into the fluidized bed reactor.

3. The method for producing polyoxymethylene dimethyl ethers according to claim 1, wherein feeding dimethoxymethane and paraformaldehyde includes pumping the dimethoxymethane into the fluidized bed reactor, and feeding solid paraformaldehyde into the fluidized bed reactor by switching screw feeders using at least two screw feeders.

4. The method for producing polyoxymethylene dimethyl ethers according to claim 1, wherein the dimethoxymethane to paraformaldehyde mass ratio is in range of 10:1 to 1:2.

5. The method for producing polyoxymethylene dimethyl ethers according to claim 1, wherein the fluidized bed reactor is a multi-stage fluidized bed reactor.

6. The method for producing polyoxymethylene dimethyl ethers according to claim 1, wherein in the synthetic reaction process, a concentration of the solid acid catalyst in the fluidized bed reactor is 5%~30% by weight, operation temperature is 30-120° C., operation pressure is 0.1~1 MPa, reaction time is 0.5~6 hours.

7. The method for producing polyoxymethylene dimethyl ethers according to claim 1, wherein the solid acid catalyst is selected from a group consisting of cation exchange resin, molecular sieves, silica gel and combinations thereof.

8. The method for producing polyoxymethylene dimethyl ethers according to claim 1, wherein in the product separation process a pH value of the extraction solvent is controlled in a range of 7~9.

9. The method for producing polyoxymethylene dimethyl ethers according to claim 1, wherein in the product separation process, the extraction solvent is selected from a group consisting of methanol, ethanol, water, benzene, acetone, aqueous solution of sodium sulfite, aqueous solution of alkali, and combinations thereof.

10. The method for producing polyoxymethylene dimethyl ethers according to claim 1, wherein m is 4 or 5.

11. The method for producing polyoxymethylene dimethyl ethers according to claim 1, wherein in the product separation process, the pre-rectifying column is a packed column or plate column, with 10~50 theoretical plates, operation pressure of the pre-rectifying column is 0~0.3 MPa, a column top temperature is 40~65° C., and a column bottom temperature is 120~150° C., a reflux ratio of the overhead fraction dimethoxymethane is 0.5~3 a remainder of the overhead fraction dimethoxymethane is recycled into the fluidized bed reactor, side withdrawing position of $PODE_2$ is under the column top, the side-draw fraction $PODE_2$ is recycled into the fluidized bed reactor, and a bottom fraction is pumped into a top of the extractive rectifying column and mixed with the extraction solvent, an operation pressure of the extractive rectifying column is 0~0.3 MPa; the unconverted formaldehyde and by-products enter the extract phase, and the extract phase is separated into the extraction solvent and the unconverted formaldehyde for recycling.

12. The method for producing polyoxymethylene dimethyl ethers according to claim 1, wherein in the product separation process, the extractive rectifying column is a packed column or plate column, with 10~40 theoretical plates, a column top temperature being 90~120° C., while a column bottom temperature being 120~150° C., an extractive solvent to feedstock mass ratio is 0.3~1.5, a pH value of the extractive solvent is 6~10, a bottom fraction in the extractive rectifying column is pumped into the vacuum rectifying column, operation pressure of the vacuum rectifying column is −0.06~0.098 Mpa, in the vacuum rectifying column, a feedstock mixture is separated into an overhead fraction target components $PODE_{3\sim m}$ and heavy fraction $PODE_{(m+1)\sim n}$.

13. The method for producing polyoxymethylene dimethyl ethers according to claim 1, wherein the vacuum rectifying column is a packed column with 10~30 theoretical plates, a column top temperature being 60~100° C., and a column bottom temperature is 120~160° C.

14. The method for producing polyoxymethylene dimethyl ethers according to claim 6, wherein in the synthetic reaction process, a concentration of the solid acid catalyst in the fluidized bed reactor is 15%~30% by weight.

15. The method for producing polyoxymethylene dimethyl ethers according to claim 2, wherein the dimethoxymethane to paraformaldehyde mass ratio is in a range of 10:1 to 1:2.

16. The method for producing polyoxymethylene dimethyl ethers according to claim 2, wherein the dimethoxymethane to paraformaldehyde mass ratio is in a range of 5:1 to 1:2.

17. The method for producing polyoxymethylene dimethyl ethers according to claim 6, wherein in the synthetic reaction process, operation temperature in the fluidized bed reactor is 90~110° C.

18. The method for producing polyoxymethylene dimethyl ethers according to claim 6, wherein in the synthetic reaction process, operation pressure in the fluidized bed reactor is 0.5 MPa~0.8 MPa.

19. The method for producing polyoxymethylene dimethyl ethers according to claim 1, in the product separation process, the pre-rectifying column is a packed column or plate column, with 20~40 theoretical plates, an operation pressure of the pre-rectifying column is 0.1~0.3 MPa, a column top temperature is 50~65° C., a reflux ratio of the overhead fraction dimethoxymethane is 1~3, the heavy fraction of $PODE_{n>2}$ is drawn from a column bottom, and a column bottom temperature is 140~150° C.

20. The method for producing polyoxymethylene dimethyl ethers according to claim 1, wherein a pH value of the extraction solvent is in a range of 7~9.

\* \* \* \* \*